US012690936B2

(12) United States Patent
Turbett

(10) Patent No.: US 12,690,936 B2
(45) Date of Patent: Jul. 28, 2026

(54) STERILIZATION WRAP SYSTEM

(71) Applicant: Turbett Surgical, Inc., Henrietta, NY (US)

(72) Inventor: Robert E. Turbett, Penfield, NY (US)

(73) Assignee: Turbett Surgical, Inc., Henrietta, NY (US)

( * ) Notice: Subject to any disclaimer, the term of this patent is extended or adjusted under 35 U.S.C. 154(b) by 0 days.

(21) Appl. No.: 18/642,747

(22) Filed: Apr. 22, 2024

(65) Prior Publication Data

US 2025/0326548 A1      Oct. 23, 2025

Related U.S. Application Data

(63) Continuation of application No. 17/533,824, filed on Nov. 23, 2021, now Pat. No. 11,963,735, which is a
(Continued)

(51) Int. Cl.
*A61L 2/26* (2006.01)
*A61B 46/00* (2016.01)
(Continued)

(52) U.S. Cl.
CPC .............. *A61B 46/40* (2016.02); *A61B 46/10* (2016.02); *A61B 50/13* (2016.02); *A61B 50/15* (2016.02);
(Continued)

(58) Field of Classification Search
CPC ......... A61B 46/10; A61B 46/40; A61B 50/13; A61B 50/15; A61B 50/33; A61B 50/36;
(Continued)

(56) References Cited

U.S. PATENT DOCUMENTS 4,051,845 A    10/1977  Collins
4,166,461 A     9/1979  Oliver et al.
(Continued)

FOREIGN PATENT DOCUMENTS

AU      2003208110 B2    7/2003
CN         1648011 A    8/2005
(Continued)

OTHER PUBLICATIONS

Kraton Corporation "Product Finder," [retrieved on Jul. 19, 2023]. Retrieved from the Internet <URL https://kraton.com/productfinder/_gl=1*2fie2e*_up*MQ..*_ga*MjYzODQyOTU1LjE2ODkzNjkwMDY.*_ga_ZRJ064KN1J*MTY4OTM2OTAwNS4xLjEuMTY4OTM2OTIxMi4wLjAuMA>, 3 pages.
(Continued)

*Primary Examiner* — Timothy C Cleveland
(74) *Attorney, Agent, or Firm* — Harter Secrest & Emery LLP; Jodi A. Reynolds

(57) ABSTRACT

The present invention comprises a sterilizing wrap system comprising a base having a support surface and a first sealing surface spaced from the support surface, the support surface supports at least one object requiring sterilization. A wrap is sized to engage the first sealing surface of the base to define a volume encompassing the support surface and the spaced first sealing surface of the base. A first seal maintains a sealed interface between the wrap and the first sealing surface.

21 Claims, 12 Drawing Sheets

Related U.S. Application Data continuation of application No. 16/040,058, filed on Jul. 19, 2018, now Pat. No. 11,185,383.

(60) Provisional application No. 62/534,494, filed on Jul. 19, 2017.

(51) Int. Cl.

| | |
|---|---|
| *A61B 46/10* | (2016.01) |
| *A61B 50/13* | (2016.01) |
| *A61B 50/15* | (2016.01) |
| *A61B 50/33* | (2016.01) |
| *B65B 11/00* | (2006.01) |
| *B65B 55/02* | (2006.01) |
| *B65D 65/22* | (2006.01) |
| *A61B 50/00* | (2016.01) |
| *A61B 50/30* | (2016.01) |
| *A61B 50/36* | (2016.01) |
| *A61L 2/07* | (2006.01) |
| *A61L 2/08* | (2006.01) |
| *A61L 2/14* | (2006.01) |
| *A61L 2/206* | (2026.01) |
| *A61L 2/208* | (2026.01) |
| *A61L 103/00* | (2026.01) |
| *A61L 103/15* | (2026.01) |

(52) U.S. Cl.
    CPC ............... *A61B 50/33* (2016.02); *A61L 2/26* (2013.01); *B65B 11/004* (2013.01); *B65B 55/02* (2013.01); *B65D 65/22* (2013.01); *A61B 2050/005* (2016.02); *A61B 50/30* (2016.02); *A61B 2050/314* (2016.02); *A61B 50/36* (2016.02); *A61L 2/07* (2013.01); *A61L 2/08* (2013.01); *A61L 2/14* (2013.01); *A61L 2/206* (2013.01); *A61L 2/208* (2013.01); *A61L 2103/15* (2026.01); *A61L 2103/23* (2026.01); *A61L 2202/181* (2013.01); *A61L 2202/182* (2013.01)

(58) Field of Classification Search
    CPC ....... A61B 2050/314; A61L 2/07; A61L 2/08; A61L 2/14; A61L 2/206; A61L 2/208; A61L 2/26; A61L 2202/181; A61L 2202/182; A61L 2202/23; A61L 2202/24
    See application file for complete search history.

(56) References Cited

U.S. PATENT DOCUMENTS

| | | | |
|---|---|---|---|
| 6,189,459 | B1 | 2/2001 | DeAngelis |
| 6,440,375 | B1 | 8/2002 | Davis et al. |
| 6,572,819 | B1 | 6/2003 | Wu et al. |
| 8,454,901 | B1 | 6/2013 | Snyder, III |
| 10,543,054 | B2 | 1/2020 | Houde et al. |
| 10,987,438 | B2 | 4/2021 | Turbett |
| 2003/0056698 | A1 | 3/2003 | Comeaux |
| 2004/0194673 | A1 | 10/2004 | Comeaux et al. |
| 2006/0260515 | A1 | 11/2006 | Hodges et al. |
| 2007/0026472 | A1 | 2/2007 | Prokash et al. |
| 2010/0154353 | A1 | 6/2010 | Cesa et al. |
| 2011/0079535 | A1 | 4/2011 | Prokash et al. |
| 2011/0139650 | A1 | 6/2011 | Dworak |
| 2013/0042576 | A1 | 2/2013 | Sweeney |
| 2014/0216305 | A1 | 8/2014 | Hodges et al. |
| 2015/0096475 | A1 | 4/2015 | Lee et al. |
| 2015/0314026 | A1 | 11/2015 | Mauzerall et al. |
| 2016/0310226 | A1 | 10/2016 | Grindstaff |
| 2020/0060780 | A1 | 2/2020 | Bemman et al. |
| 2022/0079700 | A1 | 3/2022 | Turbett et al. |

FOREIGN PATENT DOCUMENTS

| | | | |
|---|---|---|---|
| CN | 104220100 | A | 12/2014 |
| CN | 106458441 | A | 2/2017 |
| JP | 2001-120574 | A | 5/2001 |
| JP | 3186961 | U | 10/2013 |
| JP | 2015-528324 | A | 9/2015 |
| WO | 2006038978 | A1 | 4/2006 |
| WO | 2018183794 | A1 | 10/2018 |

OTHER PUBLICATIONS

Standard et al. (1971) "Microbial Penetration of Muslin-and Paper-Wrapped Sterile Packs Stored on Open Shelves and in Closed Cabinets," Applied Microbiology 22(3):432-437.

European Patent Office, Extended European Search Report for corresponding EP Application No. 18835824.6, dated Feb. 24, 2021.

Korean Intellectual Property Office (ISA/KR), International Search Report and Written Opinion from corresponding PCT Appl. No. PCT/US18/42884, mailed and completed Jan. 3, 2019.

LJ Star Incorporated. "Precision-Made Hygienic Clamps for Pharmaceutical & Biotech 11, 23 Industries" Product Datasheet (online). Dec. 2018; Retrieved from the Internet on Oct. 10, 2023: <URL: https://www.alphacontrols.com/Multimedia/www.alphacontrols.com/Files/ProductCategory/268/sanitary-clamp-fittings-overview.pdf>.

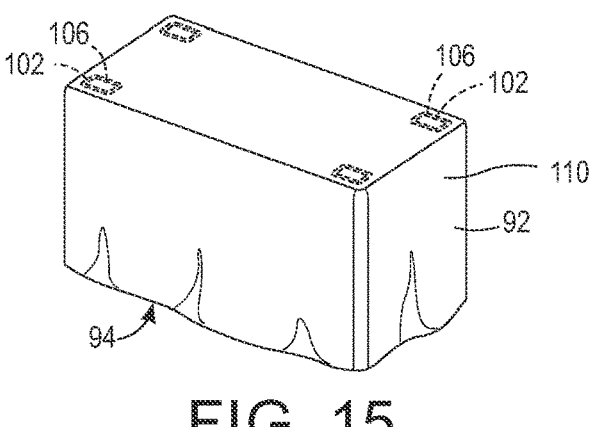
FIG. 15
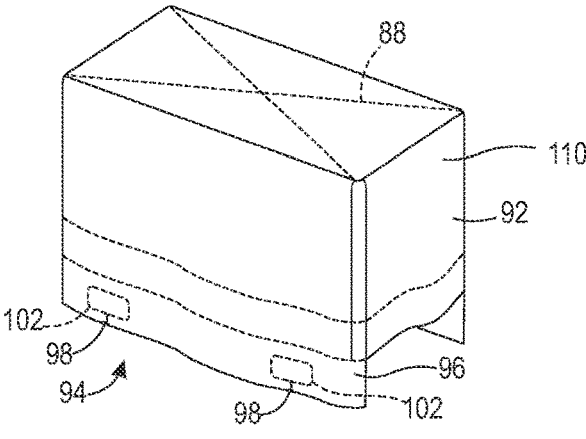
FIG. 16
FIG. 17

STERILIZATION WRAP SYSTEM

CROSS-REFERENCE TO RELATED APPLICATIONS

This application is a continuation of U.S. patent application Ser. No. 17/533,824 filed Nov. 23, 2021, which issued as U.S. Pat. No. 11,963,735; which is a continuation of U.S. application Ser. No. 16/040,058 filed on Jul. 19, 2018, which issued as U.S. Pat. No. 11,185,383 on Nov. 30, 2021; which claims the benefit of U.S. Provisional Patent Application No. 62/534,494 filed Jul. 19, 2017, each of which is hereby incorporated herein by reference in its entirety.

BACKGROUND OF THE INVENTION

1. Field of the Invention

The present invention relates to a method and apparatus for sterilizing surgical instruments and the like and more particularly to a sterilizing wrap system comprising a base and a wrap.

2. Description of Related Art

Cleaning and sterilizing surgical instruments, laboratory supplies, and medical devices are important in many fields including, but not limited to, scientific research, veterinary medicine, and human medicine. Surgical instruments, for example, must be provided in a sterile condition to be able to be used in surgery. To reduce the risk of introducing harmful microorganisms to a patient or in scientific research, several steps are typically followed. First, the objects may be decontaminated and pre-cleaned. Next, the objects are cleaned, rinsed and dried. Following a thorough cleaning, the objects are sterilized. Sterilization is a term referring to any process that eliminates, removes, deactivates, or kills bacteria or other types of living microorganisms, including transmissible agents (such as fungi, bacteria, viruses, or spore forms) present on a surface, or contained in a fluid, or in medication, or in a compound such as biological culture media. Sterilization can be achieved by applying heat, steam, chemicals, such as using ethylene oxide (EO), irradiation, high pressure, and filtration or combinations thereof. In general, surgical instruments, laboratory supplies, and medical devices must be sterilized to a high sterility assurance level before use on a body. Examples of such instruments include scalpels, hypodermic needles, endoscopes, and implantable medical devices (IMD), such as artificial pacemakers.

A widely used method for heat sterilization is the autoclave, sometimes referred to as a converter. Autoclaves commonly use steam heated to 121-134° C. To achieve a degree of sterility, a holding time of at least 15 minutes at 121° C. at 100 kPA, or 3 minutes at 134° C. at 100 kPa is required. Additional sterilizing time is usually required for liquids and instruments packed in layers of cloth, as they may take longer to reach the required temperature.

One method of sterilization involves passing steam through a rigid container system, for example, a cabinet. For effective sterilization, steam needs to penetrate a cabinet load uniformly. Accordingly, the cabinet must not be overcrowded, and the lids of bottles and containers must be left ajar. During the initial heating of the chamber, residual air must be removed. Indicators should be placed in the most difficult places for the steam to reach to ensure that steam actually penetrates there.

A filter is typically placed over the vent to keep particles or extraneous materials from entering the cabinet before, during or after the sterilizing process. Once the sterilizing process is completed the filter needs to be removed and inspected by medical professionals to verify the integrity of the sterilizing process was maintained. If it is discovered during inspection that the filter did not remain intact, the sterilizing process has to be repeated with a new filter.

Another method of sterilization involves wrapping instruments, supplies, medical devices, or trays containing such objects, with a packaging material to allow sterilization of the contents of the tray, and to maintain the sterility of the tray contents until the wrap is opened. Traditionally, instruments that need to be reprocessed are provided in vented trays, allowing the sterilizing agent to flow through the tray, and sterilizing all the surfaces. In order to maintain sterility after removal from the sterilizer, the trays are wrapped in a material that allows the sterilizing agent to pass through, but protecting the inner tray from microorganisms until use. A multitude of packaging materials can be used for sterilization, including woven fabrics, which may be made of cotton, a cotton-polyester blend, or synthetic blend, or nonwoven materials, which may be made of plastic polymers, cellulose fibers, or washed paper pulp bonded under pressure into sheets. Wrapping instruments, supplies, medical devices, or trays containing such objects, in packaging material, including but not limited to wraps sometimes results in the packaging material tearing or puncturing, in which case the sterilization process must be repeated with new packaging material. Single instruments can be individually sterilized in a peel pouch. The pouch maintains the sterility of the instrument after the sterilization process is complete by protecting it from the contaminants in the environment. Peel pouches, however, are not efficient as multiple tools cannot be sterilized within the same peel pouch. Further, peel pouches are to be loaded into a sterilizer on its size to promote air removal and penetration of the sterilant as well as to discourage moisture retention. Peel pouches cannot include implants having several component parts. These component parts would need to be packaged in separate peel pouches before sterilizing, typically by gamma irradiation processing.

Alternatively, the trays may be placed in a rigid container utilizing filters that act as the wrap does, allowing the sterilizing agent in, but blocking microorganisms afterwards. The filter also allows the escape of the sterilizing agent or its byproducts. Once the sterilizing process is complete the filter needs to be removed and inspected by medical professionals to verify the integrity of the sterilizing process was maintained. If it is discovered during inspection that the filter did not remain intact, the sterilizing process has to be repeated with a new filter. Large containers have been made to handle multiple trays to allow a consolidation of steps, simplifying the process. These large containers are expensive to manufacture, however, and bulky to store. Further, the large containers hold several instruments, which collectively, is a significant weight load, requiring particular lifting devices to load and unload the container into a sterilizer and to place the container in storage.

BRIEF SUMMARY OF THE INVENTION

The present invention includes a sterilizing wrap system for sterilization comprising a base having a support surface and a first sealing surface spaced from the support surface, the support surface for supporting at least one object requiring sterilization, a wrap sized to engage the first sealing surface of the base to define a volume encompassing the support surface and the spaced first sealing surface of the base, and a first seal for maintaining a sealed interface between the wrap and the first sealing surface.

The present invention further includes a sterilizing wrap system for sterilization. The sterilizing wrap system includes a base having a support surface for supporting at least one object requiring sterilization and a first sealing surface, and a wrap sized to at least partially encompass the base, the wrap having a first portion for encompassing the support surface of the base and a second portion for confronting the first sealing surface of the base, wherein the second portion is a flexible collar for expanding to dispose the wrap over the support surface of the base in the install position and for applying tension to the first sealing surface of the base in the deployed position.

Another configuration of the present invention provides a method of packaging objects for sterilization. The method includes placing at least one object to be sterilized on a support surface of a base, the base having a first sealing surface; deploying a wrap having a first portion for encompassing the support surface of the base and a second portion for confronting the first sealing surface of the base; and clamping the second portion of the wrap to the first sealing surface of the base to form a sealed interface between the wrap and the first sealing surface in a deployed position. The method may further include the step of applying a frame having vented areas before the step of deploying the wrap.

In a configuration, the method further includes the step of transporting the base having the deployed wrap to a sterilizer; transferring the base having the deployed wrap into the sterilizer; performing a sterilization cycle in the sterilizer; removing the base having the deployed wrap from the sterilizer; transporting the base having the deployed wrap to the area of use; and opening the deployed wrap to expose the at least one object sterilized in the sterilizer. Further, the step of transporting the base having the deployed wrap to the sterilizer may further include loading the base having the deployed wrap onto a transfer cart, the transfer cart having a first end including a locking mechanism and a second end; releasably locking the base having the deployed wrap to the transfer cart; positioning the first end of the transfer cart adjacent the sterilizer; and locking the first end of the transfer cart to the sterilizer with the locking mechanism and releasing the lock between the base having the deployed wrap and the transfer cart to enable the base having the deployed wrap to be transferred into the sterilizer.

In yet another configuration, a single-use wrap system for use in the sterilization of objects requiring sterilization includes a rigid base formed of a material adapted to withstand exposure to a sterilizing agent without degradation, the base having a support surface having a portion for retaining objects and a perimeter edge; a wrap sized to overlap the support surface and having a perimeter edge corresponding with the perimeter edge of the support surface of the base; and a seal disposed along the perimeter edges of the wrap and/or the base, the seal forming a sealed interface between the wrap and the base. The support surface may be removeable from the base.

BRIEF DESCRIPTION OF THE SEVERAL VIEWS OF THE DRAWING(S)

FIG. 15 is a perspective view of the sterilizing wrap configured to encapsulate the table shown in FIG. 18

FIG. 16 is a perspective view of the sterilizing wrap configured to encapsulate a table having a pedestal.

FIG. 17 is perspective view of another sterilizing wrap of the present invention.

DETAILED DESCRIPTION OF THE INVENTION

It should be appreciated that the same reference numbers appearing in different figures identify the same structural elements of the present invention. While the description of the present invention includes what is currently considered to be the preferred configurations, it should be appreciated that the present invention is not limited to such configurations. Moreover, it should be appreciated that the present invention is not limited to the particular methodology, materials and modifications described herein and that the terminology used herein is not intended to limit the scope of the present invention. The scope of the present invention is therefore to be determined solely by the appended claims.

The invention pertains to a sterilizing wrap system to provide significant vent to volume ratios for purposes of sterilizing instruments, medical devices, and the like during sterilization in a sterilizer. The term sterilizer includes, but is not limited to, a housing or device defining an interior retaining the sterilization system and in which a controlled environment is create to impart a desired sterilization. Sterilizers include autoclaves; hot air ovens; ethylene oxide; low temperature steam and formaldehyde; sporicidal chemicals; irradiation; chlorine dioxide (CD) gas sterilization; hydrogen peroxide; vaporized hydrogen peroxide; hydrogen peroxide plasma; electron beam and gas plasma devices.

The system provides the benefits of both wrapping techniques and rigid container systems. By utilizing a base as a rigid component without a door, one or more instruments and/or trays may be placed on it. By utilizing a wrap as a protective cover, significant vent to volume effects can be realized. This results in a shorter time required for the sterilizing agent or its byproducts to be vented. Further, when a base, such as an operating room back table, is used, there is no need to transfer the instruments from a rigid container or tray onto a back table for use in the operating room, as the back table is integral to the sterilizing wrap system and thus, the instruments are already organized on the table and presentable after sterilization. By "operating room back table" or "back table" it is meant to generally refer to a table used in the operating room for holding surgical instruments. The operating room back table is sometimes known as an instrument table or a work table. The back table can be made of stainless steel, plastic, or other rigid materials, and can be any shape or size. Typically, the back table is a rectangular shaped table having legs and/or a pedestal which may or may not be adjustable and/or removable.

Figure 1:
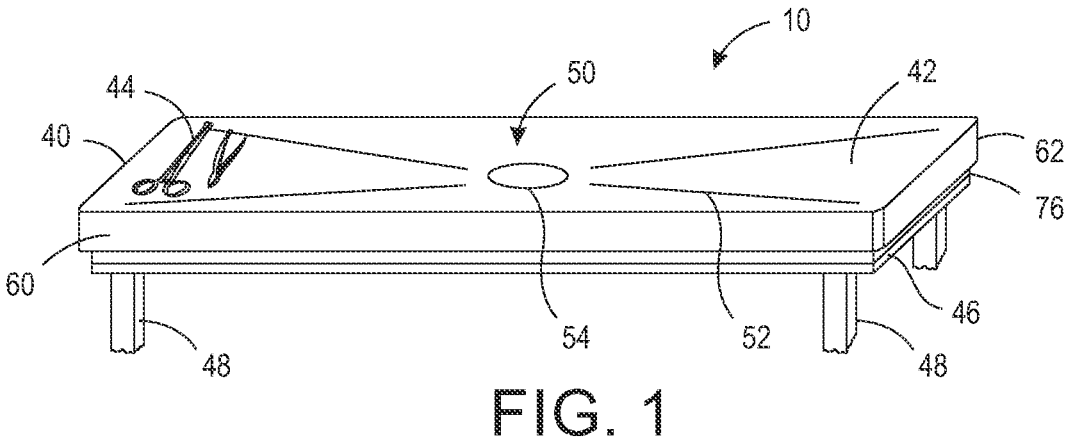
FIG. 1 is a perspective view of an operating back room table.
Figure 2:
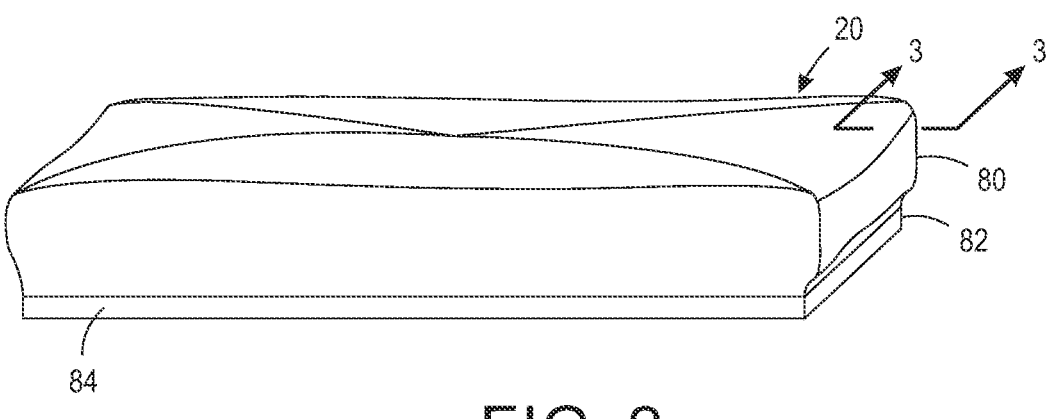
FIG. 2 is a perspective view of a sterilizing wrap configured to encompass the operating room back table.

Generally, the sterilizing wrap system 100 includes a base 10 providing a support surface and a wrap 20 providing a protective cover. The base 10 may be any shape and size for providing a support surface. For example, although base 10 is shown in a rectangular configuration, the base 10 may be any shape, including, but not limited to, circular, oval, square, and elliptical. The base 10 in this configuration is rigid and may be a tray, table, sheet, plate, or any other type of rigid, supportive base. It should be appreciated that the sterilization wrap 20 may take many different shapes and forms, including but not limited to a sheet, bag, pouch, and a partially formed bag. Referring now to the figures, FIG. 1 is a perspective view of one configuration of a base 10 and FIG. 2 is a perspective view of one configuration of a wrap 20. As shown in FIG. 1, the sterilizing wrap system 100 includes base 10, which in one configuration may be an operation room back table 40 having a support surface 42 for supporting at least one object 44 requiring sterilization by a sterilizer. Objects 44 requiring sterilization may include, but are not limited to surgical tools and instruments, implants, laboratory supplies, and medical devices. In one configuration, the base 10 includes a dependent skirt 46 and may be detachable from legs 48 or a pedestal (not shown). The base 10 may also include a flange or sidewalls (not shown) along the perimeter edge of the support surface 42 for retaining the objects 44 on the support surface 42, especially during transportation when objects may otherwise shift. Alternatively, or additionally, the base 10 may include dividers, shelves, or sectioned portions for maintaining objects 44, including but not limited to, surgical instruments and/or trays, on particular sections of the base 10. The base 10 may further include additional fasteners, including but not limited to Velcro, magnets, and the like to releasably hold the objects 44 in place. The base 10 may include a laser outline of at least some objects 44 identifying a preferred location for particular objects. Other features for organizing and maintaining objects 44 on the base 10 are intended to be included within the scope of the invention as claimed.

Figure 11:
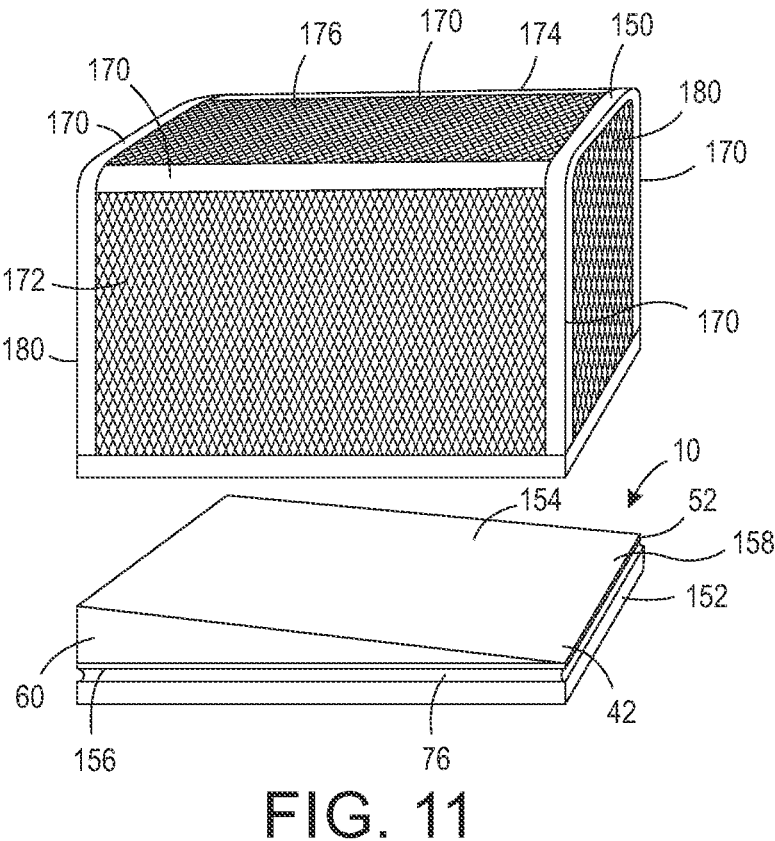
FIG. 11 is a perspective view of another exemplary embodiment of a sterilizing wrap system for sterilizing objects, the sterilizing wrap system having a base and a frame.

In some configurations, the base 10 may include a drain system 50 for draining sterilizing agent and/or liquid condensate formed during the sterilization process. The base 10 may include, for example, a sloped surface 52, for example, as shown in FIGS. 1 and 11, to direct drainage to a predetermined area. The sloped surface 52 may be of any slope and may be a straight line (angular) or curved. In one configuration the base 10 includes at least one drainage well having a downwardly sloping surface 52 arrange to direct condensate to a drain aperture 54. In one configuration, the drain aperture 54 is approximately 0.5 to 5 inches in diameter. In another configuration, the drain aperture 54 is approximately 2-3 inches in diameter. The drain aperture 54 may be any shape and size that allows liquid condensate or liquid sterilant to drain from the surface of the base 10. The surface 52 may be frusto-conical shaped to further direct sterilizing agent and condensate to the drain aperture 54. Alternatively, the drain system 50 may include a continuous decline directing sterilizing agent and/or liquid condensate to a drain well or aperture 52 located proximate one side of the base 10. It should be appreciated that the drain well or aperture 54 or a plurality of drain wells and/or apertures 52 may be positioned anywhere on the floor of the base, with the floor configured to permit drainage thereto. In yet another configuration, the drain system 50 may include a sloped surface or decline without a drain well or aperture 52, which directs sterilizing agent and/or liquid condensate to an edge of the floor of the base 10. The drain system 50 many include a filter or filters within the aperture. It should be appreciated by those having ordinary skill in the art that other drainage systems that allow for sterilizing agent and/or liquid condensate to drain from the floor of the base 10 are possible and these modifications are intended to be included within the scope of the claims. The base 10 may further include a holder to maintain the objects 44 above the drain system 50. The holder may be, for example, a plate having perforations, apertures, or wells, or a tray configured to be suspended above the base 10, among other things. The holder may be integral to the base 10 or removeable from the base 10. It should be appreciated that there are many configurations known in the art to hold instruments above a drain system and these configurations are intended to be included within the spirit and scope of the claims.

Figures 3, 4:
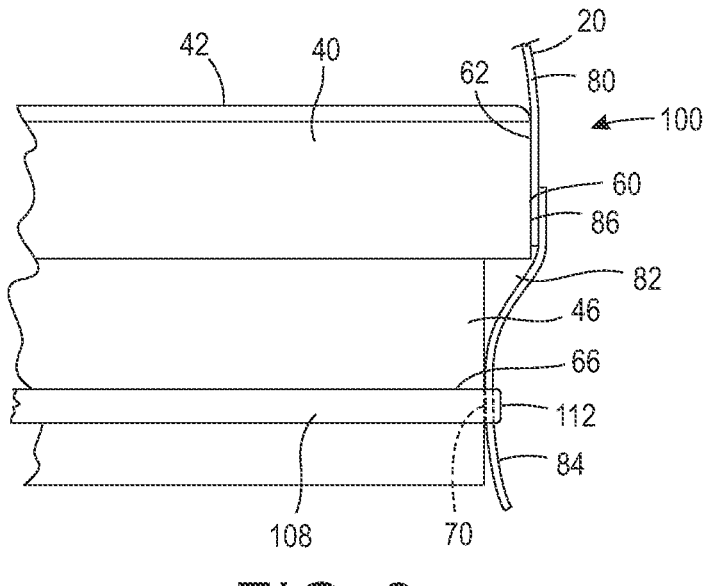
FIG. 3 is a cross-sectional view taken along lines 3-3 showing the sterilizing wrap disposed on the operating back room table and constructed of a first material and a second material.
FIG. 4 is a cross-sectional view showing the sterilizing wrap disposed on the operating back room table and constructed of a single material.
Figure 10:
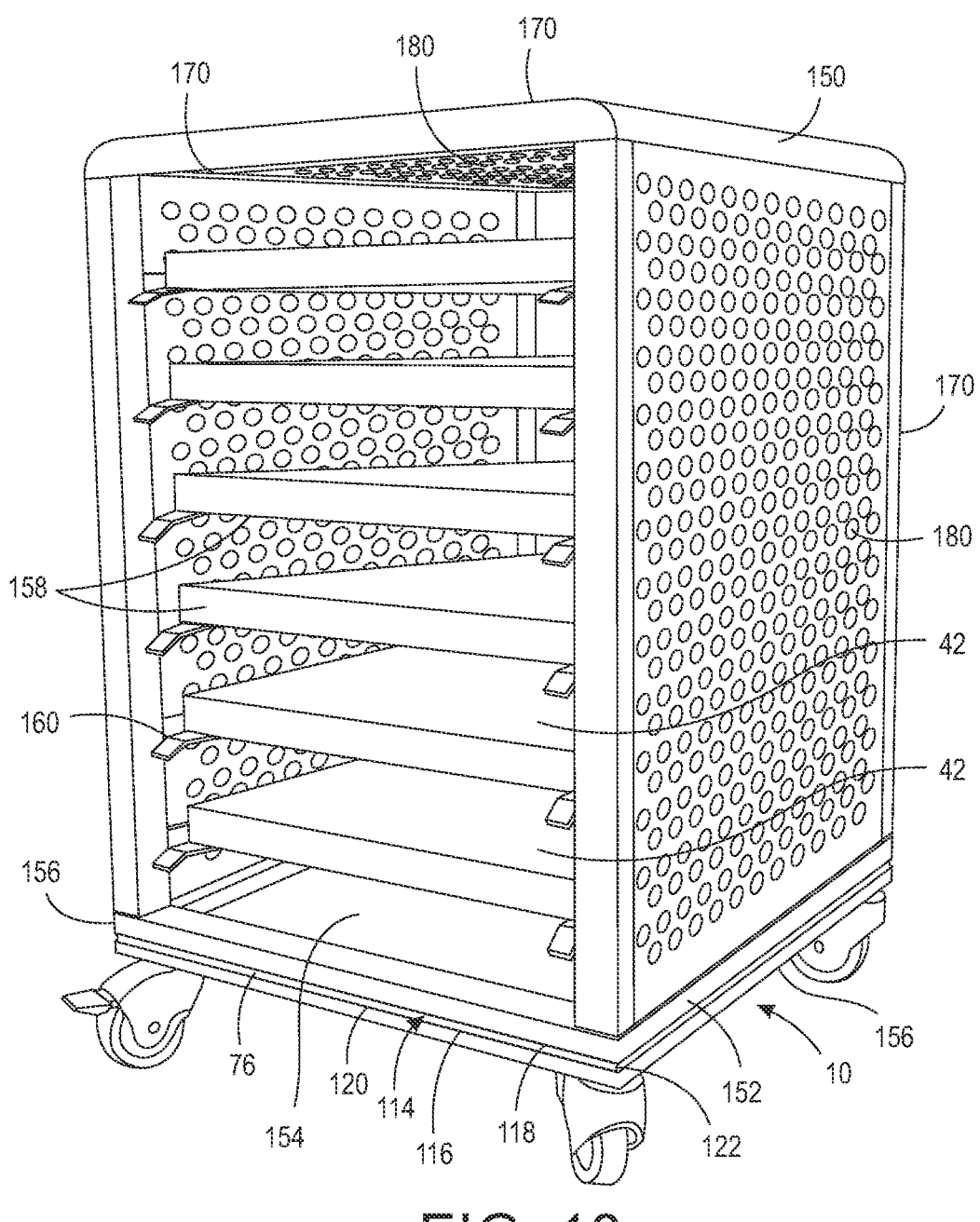
FIG. 10 is a perspective view of another exemplary embodiment of a sterilizing wrap system for sterilizing objects, the sterilizing wrap system having a base and a frame.

As shown in FIGS. 3 and 4, the base 10 further includes a sealing surface 60 for the wrap 20 to seal thereto. In one configuration, the sealing surface 60 is a lower outer wall 62 extending from a perimeter edge of the support surface 42. In another configuration, the sealing surface 60 is an upper outer wall extending above the perimeter edge the support surface 42. Typically, base 10 is comprised of stainless steel, and thus the sealing surface 60 is typically stainless steel. It should be appreciated, however, that base 10 may be comprised of other types of materials that can withstand exposure to a sterilizing agent without degradation, and thus the sealing surface 60 is not limited to such material. The base 10 may further include, or alternatively include, additional sealing surfaces, for example, sealing surface 70. In one configuration, the sealing surface 70 may include a channel 76, as shown in FIGS. 10 and 11, which channel 76 at least partially circumscribes the sealing surface 70 as described infra. In one configuration, the channel 76 circumscribes the entire perimeter of the base 10. It should be appreciated that the base 10 may have additional or alternative sealing surfaces for forming a sealed interface with the sterilizing wrap 20.

The sterilization wrap 20 may comprise many various shapes and styles and may be applied over the support surface 42 of the base 10 or from under the support surface 42 of the base 10. As shown in FIG. 2, the sterilization wrap 20 may include portion 80 for encompassing at least the support surface 42 and a portion 82 having an area for encompassing the at least the sealing surface 60 and/or 46 of the base 10. In one configuration, the wrap 20 is comprised of a material that is resistant to tears. The sterilization wrap 20 may be a single layer or multi-layer material. The material may be made with spunbound, meltblow, spunbound laminate (SMS) fabric, polypropylene, Tyvek, or any other type of material that provides a filtration capability. The materials may alternatively be one that can withstand gamma radiation. For example, the material may comprise a material that is gas-impermeable and which provides a strong and durable sterile barrier. In yet another configuration, the material is gas and water vapor permeable but not permeable by liquid. In this configuration, the material allows air and steam to pass through, but not by liquid droplets.

The wrap 20 material is selected based on the desired filtering and the type of sterilization process used. For example, a Tyvek and plastic combination would not be used in a steam sterilization process as it would melt. However, Tyvek and plastic combinations can be used in ethylene oxide (EtO) sterilizers. A filtering material can be used when steam must penetrate the material. In some configurations, the sterilization wrap 20 is a single-use material, and in other configurations, the sterilization wrap 20 is reusable. Further, the sterilization wrap 20 may include a single type of material or be constructed of multiple materials. As shown in FIG. 3, in one configuration, portion 80 is comprised of a filtering material and portion 82 is comprised of a stretchable material capable of forming an integral flexible collar 84. The flexible collar 84 may be coupled to portion 80 by ultrasonic welding, adhesive, tape, or by other manufacturing methods known in the art. In one configuration, the flexible collar 84 is made of shrink wrap that will shrink during the sterilization process to form a seal around base 10. In another configuration, the flexible collar 84 is made of non-latex, stretchable material, such as Kraton™ from Kraton Corporation available at http://www.kraton.com/products/medical/fabrics.php.

Also, the wrap 20 may be used as a protective drape as traditionally used in the operating room. Thus, the wrap 20 may be applied to the operating base 10 having objects for sterilization, wherein portion 82 is sealed to the sealing surface 60 and/or 46 of the base 10, the base 10 placed into the sterilizer and sterilized, and then transported to the operating room. The sterilized objects 44 can be accessed by opening the wrap 20 in a manner that permits the wrap to drape down from the sealing surface 60 of the base 10, such that the sterilized objects 44 are then presented to the user. The wrap 20 thus, serves as a drape in the operating room or other sterilized environment. The drape may be solid or made up of segments. The segments may be of the same material, or varied, including, but not limited to, thicker material or clear portions. In one configuration, portion 80 includes a openable portion that enable a user to open selected areas of portion 80. The openable portions may include, but are not limited to, frangible portions, perforations, cutting guide lines, scores, embossments, seams, or combinations thereof. It should be appreciated that the wrap 20 may be configured in a variety of ways so that it may be opened in a variety of fashions; it may be folded, rolled closed, designed to be torn open or creased, among other things. Alternatively, the wrap 20 may be completely removed from the base 10. The wrap 20 may be a single wrap layer or multiple wrap layers. Further, a protective liner, including, but not limited to a filter sheet may be disposed within the wrapped volume to further reduce the risk of contamination. Towels may also be used to wrap the base 10 to reduce the risk of contamination and tearing or puncturing the wrap 20.

Figure 5:
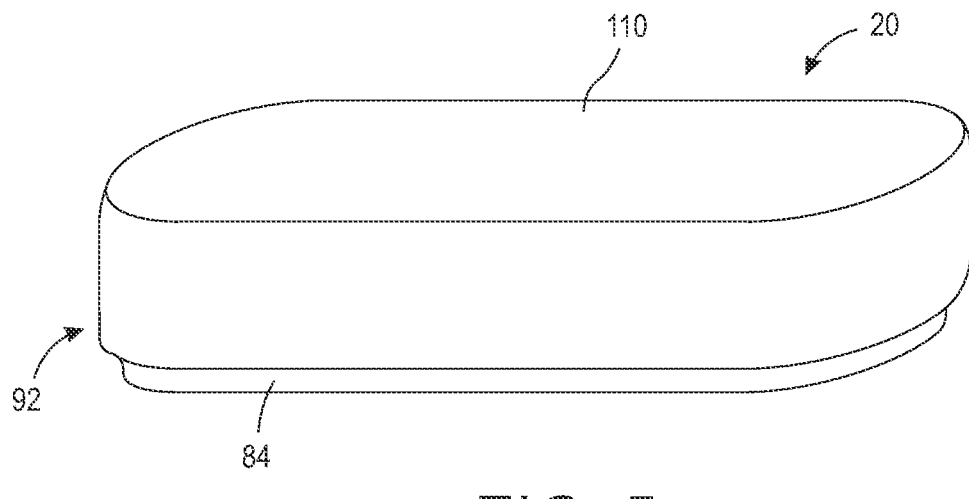
FIG. 5 is a perspective view of an exemplary embodiment of a continuous sterilizing wrap.
Figure 6:
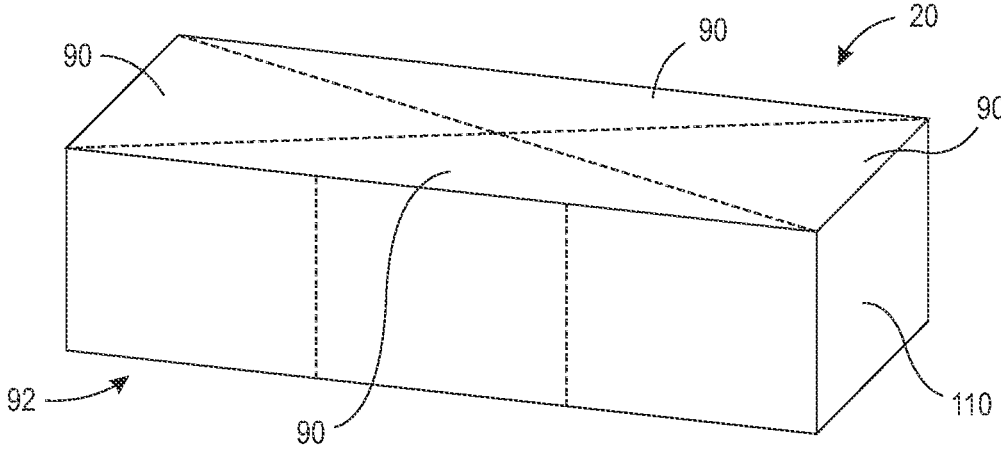
FIG. 6 is a perspective view of another exemplary embodiment of a segmented sterilizing wrap.
Figure 13:
FIG. 13 is a perspective view of another exemplary embodiment of a sterilizing wrap.
Figure 14:
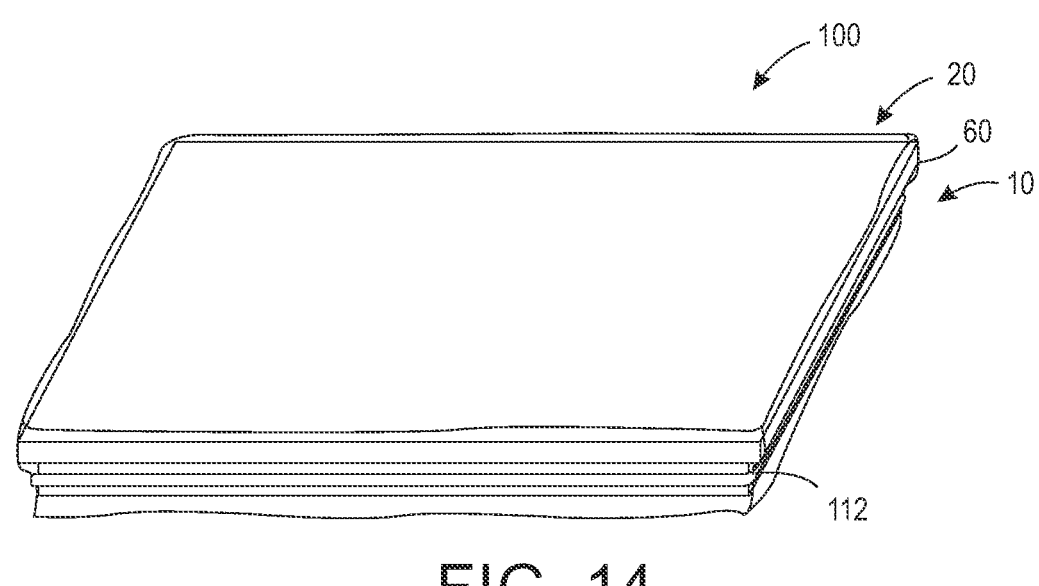
FIG. 14 is a perspective view of the sterilizing wrap sealed to an exemplary embodiment of the base.

As shown in FIG. 5, the sterilization wrap 20 may be formed of a continuous material or as shown in FIG. 6, formed with segments 90 of the same or different material. The segments 90 may be sealed with at least one sealant, including but not limited to, tape, adhesive, sealant polymer, Velcro, etc. It should be appreciated that the sterilization wrap 20 may take many different shapes and forms, including but not limited to a bag 92 defining a cavity and capable of being sealed to itself or the base 10, a sheet 182 (as shown in FIGS. 13 and 14), or a partially formed bag. The bag 92 may include a flexible collar 84 for expanding to dispose the wrap over the sealing surface 60 of the base 10 during the deployment process and applying tension to the first sealing surface of the base in the deployed position. Whether the sterilizing wrap 20 is applied from over the base 10 or from under the base 10, the wrap 20 may still be sealed to the base 10 as described infra.

Figure 18:
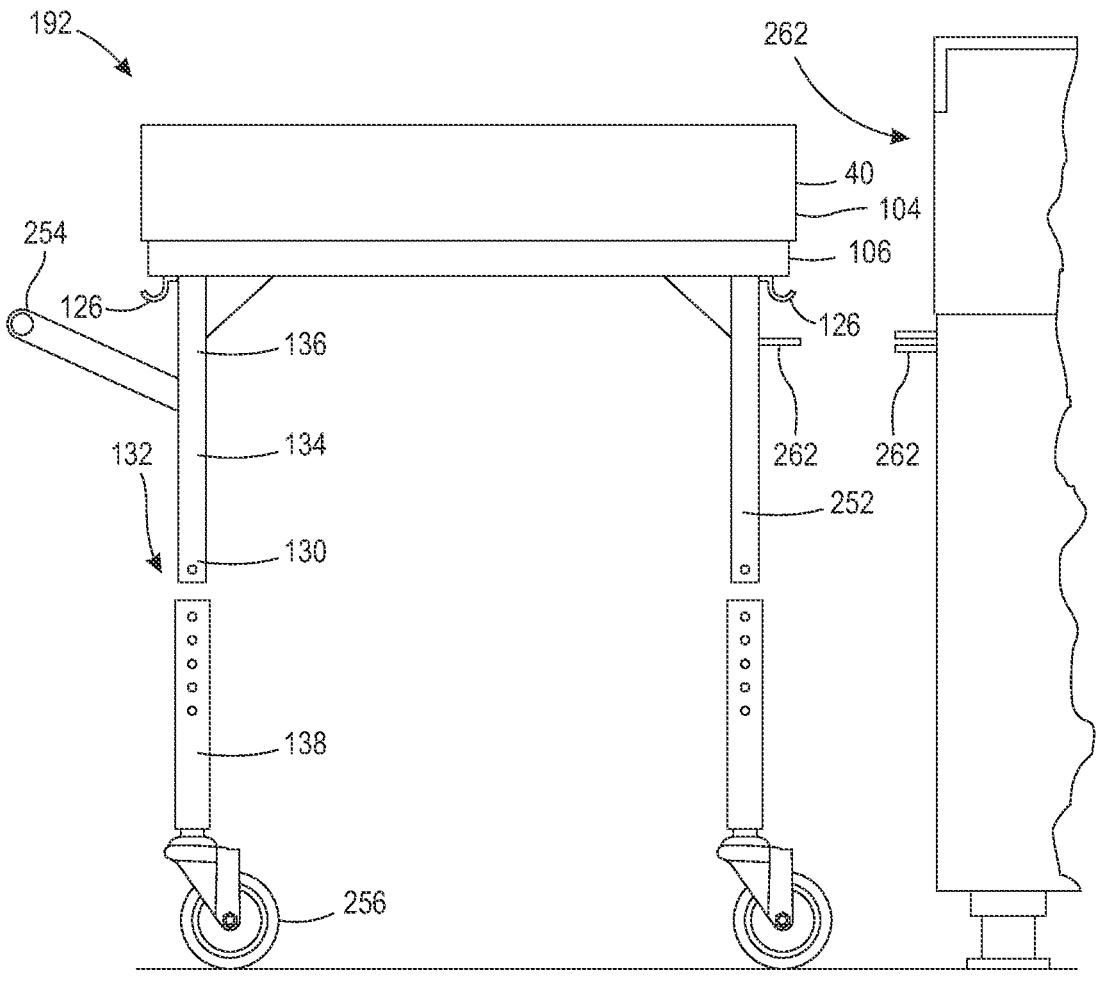
FIG. 18 is a side view of a table having detachable legs.

As shown in FIGS. 15, 16 and 17, the bag 92, in one configuration, for example, may include slots or a slot 102 for receiving a pedestal or legs 132 of the table 40. In one configuration, as shown in FIG. 18, the table 40 may disconnect from the legs 132, wherein a mouth 94 of the bag 92 having the slot or slots 102 is positioned underneath the table 40 and pulled over the table 40 such that the bag cavity encapsulates the table 40. A perimeter of the slot or slots 102 may include a seal material 106 such that a sealed interface is formed between the perimeter of the slot or slots and the underside of the table 40. In another configuration, a table 40, may include a first portion 134 of the legs 132 (or pedestal) having a first end 136 coupled to the table 40 and a second end 138 removeably coupled to a second portion 130 of the legs or pedestal. In this configuration, the slot or slots 102 of the bag 92 receive the second end 138 of legs 132, wherein a perimeter of the slot or slots 102 seal to the underside of the table 40. The upper portion of bag 92 may then be folded, taped, or otherwise made to form a seal above the table 40. In another configuration, as shown in FIG. 18, the bag 92 is positioned above the table 40 and then pulled over the table 40 such that the bag cavity encapsulates the table 40. In this configuration, the mouth 94 of the bag 92 may include a flap 96 having slots or slot 102 for receiving table legs or pedestal. The flap 96 may further include a slit 98 permitting each slot to open for receiving the leg(s) of the table 40. It should be appreciated that other configurations of the sterilization bag 92, which seal to the base around the legs or pedestal are possible and these configurations are intended to be included within the spirit and scope of the invention as claimed. The bag 92 may further include openable or frangible portions including but not limited to perforations, cutting guide lines, scores, embossments, seams, or combinations thereof. The sterilized objects 44 can be accessed by opening the bag 92 in a manner that permits the wrap 92 to drape down from at least one of the sealing surfaces 104, 106 of the base 40, such that the sterilized objects 44 are then presented to the user. The bag 92 thus, serves as a drape in the operating room or other sterilized environment.

The base may further include a catch 126 as shown in FIG. 18 for receiving the bag 92 and for holding the bag 92 in place before the bag 92 is sealed to the base 10. For example, the catch 126 may be hooks, a shoulder, or ledge positioned along the border of the base 10. Alternatively, the catch 126 may be a clamp, tape, adhesive, sealant polymer, Velcro, and the like, positioned on the base 10 or the bag 92 itself. The catch 126 restricts the movement of the bag 92 to prevent the bag 92 from moving or draping too far beneath the table.

The sterilization wrap 20 can define a venting pass through area 110 of the sterilizing wrap system 100. The venting pass through area 110 refers to the total available area for the ingress and egress of a gas, vapor, and/or liquid to and from the interior volume of the sterilizing wrap system 100. By "venting pass through area to volume ratio," it is meant the ratio of the total venting pass through area of a sterilizing wrap system 100 to the interior volume ratio of the sterilizing wrap system. This venting pass through area to volume ratio increases the area exposed to the sterilizing agent and reduces the amount of dry time required to provide no visible condensate, moisture, or sterilizing agent on the sterilized objects.

The sterilizing wrap system 100 further includes a sealed interface between the base 10 and the sterilizing wrap 20. The sealed interface between the base 10 and the sterilizing wrap may be formed by any type of mechanical or non-mechanical seal, including but not limited to a clamp, or an applied sealant, including but not limited to an adhesive, sealant polymer, or tape. In another configuration, as shown in FIGS. 3 and 4, a clamp 112 maintains a sealed interface between the sterilizing wrap 20 and the sealing surface 60 of the base 10. The clamp 112 may comprise at least one security band 108 that is received by channel 76 to form a seal that provides a barrier to entry of bacteria and particles. The channel 76 may be a conventional channel having a c-shaped or u-shaped body member 114 and an upright portion 116 with a top portion 118 and bottom portion 120 extending from the upright portion 116 to define a band-receiving notch 122, as shown in FIG. 10. In one configuration, the channel 76 has a height in the range of at least 0.25-1 inch, however, other channel sizes are possible. The security band 112 is sized to fit within the channel 76 and to provide a sealing interface between the base 10 and the wrap 20. Although the security band 112 as shown encompasses the entire perimeter of the base 10, it should be appreciated that more than one security band 112 may be used to accomplish the same. Further, it should be appreciated that other types of clamps that maintain a sealing interface between the wrap 20 and the base 10 are contemplated and these modifications are intended to be included herein. For example, shrink wrap or Krayton material may be used to form the clamp around the base 10 such that a sealed interface is maintained between the wrap 20 and the base 10.

The wrap 20 may alternatively, or additionally, include a seal 86 for forming a sealed interface between the wrap 20 and a sealing surface 60. The seal 86 may be formed of any seal that is capable of providing a sealed interface between the wrap 20 and the base 10, including but not limited to, a band, adhesive, sealant polymer, tape, and shrink-wrap. The shrink-wrap may be wrapped around the base 10 and then shrunk during the sterilization process as a result of the high heat needed for sterilization, forming a seal between the wrap 20 and the base 10. Alternatively, heat may be applied before sterilization to shrink the shrink-wrap to secure the wrap 20 to the base 10 and to form a seal between the wrap 20 and the base 10 before sterilization.

Figure 7:
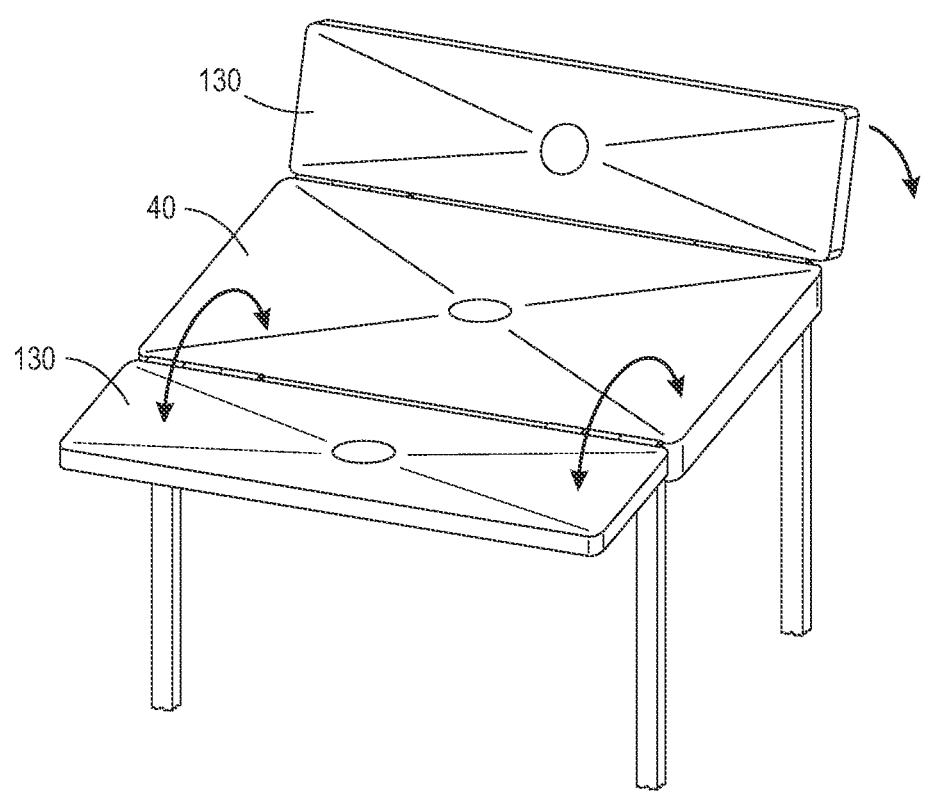
FIG. 7 is a perspective view of an exemplary embodiment of an operating back room table having extending sides.

The table 40 (or base 10) may include various configurations. For example, as shown in FIG. 7, the table 40 may include extending sides 128 to provide additional surface space to hold objects 44. The table 40 may have, for example, folding (or flip out) panels or attaching panels. In another configuration, the table 40 includes slidable panels. One reason these configurations may be preferred is to accommodate a sterilizer that is narrower than the desired base dimensions. For example, a sterilizer may have a width of 24 inches, however, the desired surface area of a base may be 30 inches or wider. To provide the desired surface area of the base, while enabling the base to fit directly into a sterilizer, the base may have such extendable or folding panels. In yet another configuration, a table may include two segments that are releasably joined together. Another configuration includes two removeable compartments that are supported on top of a base. The compartments may be releasably joined together by a fastener.

Figure 8:
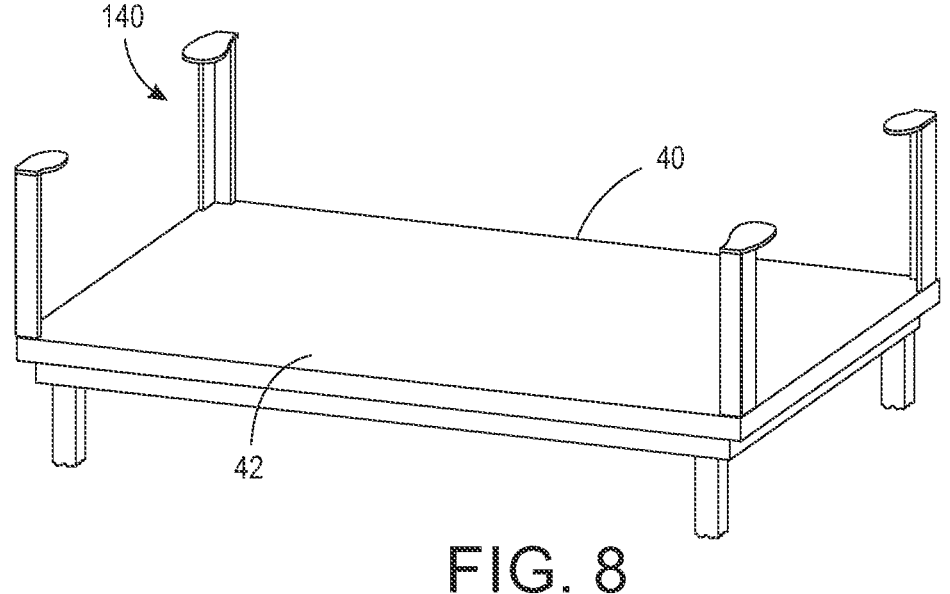
FIG. 8 is a perspective view of an exemplary embodiment of a sterilizing wrap support.
Figure 9:
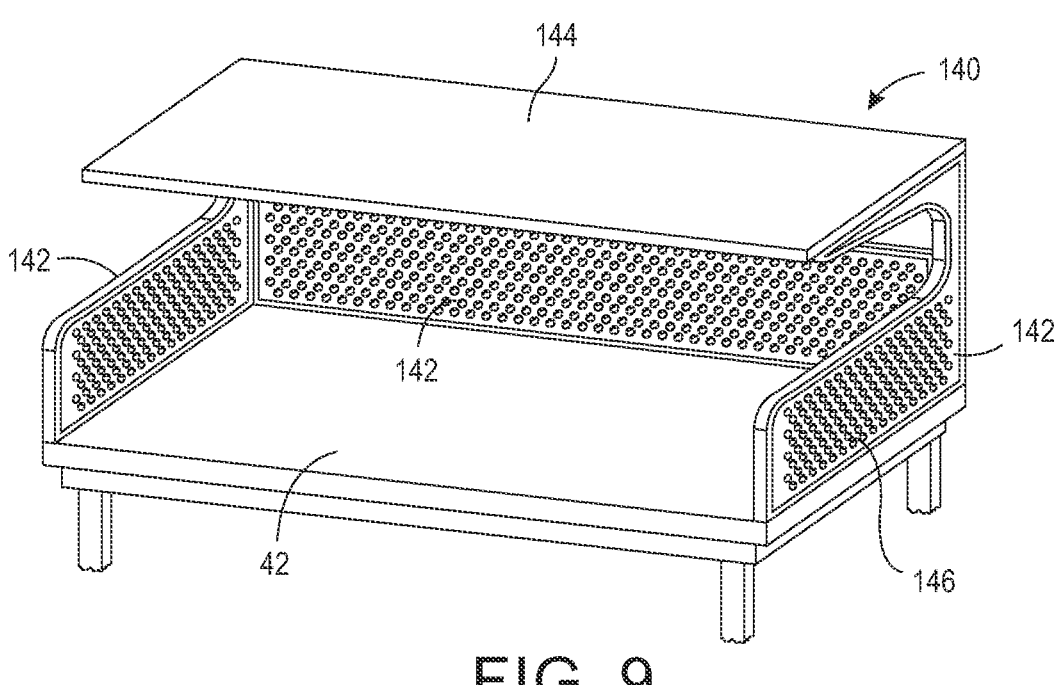
FIG. 9 is a perspective view of an exemplary embodiment of an operating back room table having support sides and a top shelf.

As shown in FIGS. 8 and 9, the table 40 may further include additional supports 140 to locate the sterilizing wrap 20 to define a volume encompassing the support surface 42 of the table 40 and to help prevent the wrap 20 from a tear or puncture from the objects 44 contained on the table 40. The supports 140 may be collapsible such that when the table 40 is in use, the supports 140 do not interfere with a user's access to the objects 44 on the table 40. In another configuration, the supports 140 are removeable. As shown in FIG. 8, the supports 140 may include an end portion 190 that bends inwardly to reduce tearing or puncturing the wrap 20. Alternatively, the end portions 190 may be capped or otherwise shaped to reduce the risk of tearing or puncturing the wrap 20. As shown in FIG. 9, the additional supports 140 include sidewalls 142 extending from the support surface 42 and a top shelf 144 spaced from the support surface 42 of the table 40. The top shelf 144 can provide a support surface for the sterilizing wrap 20. The sidewalls 142 and top shelf 144 may be vented, by apertures or openings, to permit entry of steam during the sterilization process. As shown in FIG. 9, the sidewalls 142 include a fenestrated or perforated surface 146 with numerous openings that allow for the passage of a sterilizing agent, such as steam from an autoclave during a sterilization cycle. Although three sidewalls are shown, it should be appreciated by those having ordinary skill in the art that one, two, three, or four sidewalls with any arrangement of holes, slits, or openings that allow for the passage of a sterilizing agent are possible and these modifications are intended to be included within the scope of the claims.

Referring now to FIGS. 10-13, the sterilizing wrap system 100 may include a base 10 providing a plurality of support surfaces 42 for objects 44 to be sterilized and a frame 150. In one configuration, a wrap 20 encapsulates the frame 150 providing a protective cover. As shown in FIG. 10, base 10 may include a plurality of trays 158 and/or a floor 154 as support surface 42 and sidewalls 156 extending therefrom. The floor 154 supports at least one object 44 requiring sterilization by a sterilizer. The base 10 retains the objects 44 and/or the frame 150. Alternatively, or additionally, the base 10 may include dividers, shelves, or sectioned portions for maintaining objects 44, including but not limited to, surgical instruments and/or trays, on particular sections of the base 10. As shown in FIG. 10, the sterilizing wrap system 100 may include multiple trays 158 arranged on a rack system 160. As set forth above, the base 10 may further include additional fasteners to releasably hold the objects 44 in place. The base 10 may further include a drain system 50 for draining condensate formed during the sterilization process as described supra. In the configuration shown in FIG. 11, the floor 154 is declined to direct sterilizing agent and/or liquid condensate to a predetermined area, such as a drain well or aperture. In this configuration the drain well is located proximate one side of the support surface 42. However, the floor 154 may be sloped and declined to a drain located in a different predetermined area. It should be appreciated by those having ordinary skill in the art that other drainage systems that allow for sterilizing agent and/or liquid condensate to drain from the support surface 42 of the base 10 are possible and these modifications are intended to be included within the scope of the claims The base 10 further includes a sealing surface 60 for the wrap 20 to seal thereto. In one configuration, the sealing surface 60 is located along the perimeter of the outer sidewall 156. In another configuration, the sealing surface 60 is a top edge of the sidewalls 156. In yet another configuration, the sealing surface 60 is located on the outer surface of the floor 154 (the side opposite the support surface 42). The sealing surface 60 may include a channel 76, as described infra, at least partially circumscribing the sealing surface 60. Further, more than one sealing surface 60 may be used, creating two or more sealing interfaces.

Figure 12:
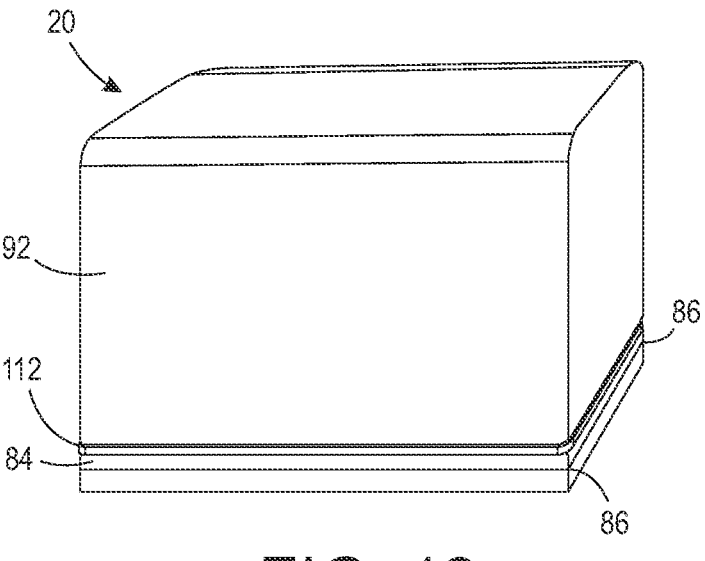
FIG. 12 is a perspective view of a sterilizing wrap configured to encapsulate the frame and base shown in FIG. 11.

Referring to FIGS. 11 and 12, the sterilizing wrap system 100 may include a frame 150 operatively connected to the tray 158. The frame 150 may be integral with the base 10 or separable as shown in FIG. 11. The frame 150 includes a plurality of struts or battens 170 forming front and back portions 172, 174, a top portion 176 and side portions 178. Each portion 172, 174, 176, 178 defines a hollow center, which may be configured to include a fenestrated or perforated surface such as screen or a panel having openings or holes, and the like. Alternatively, the hollow center may include a filter suitable for permitting passage of a sterilizing agent but resilient enough to not rip or tear during sterilization. The filter can be made of any type of porous paper, cellulose type material, or polymeric substance, such as polypropylene. The frame 150 and filter may be sealed to the base 10, thus providing a sterilizing filter system. Providing the sterilization wrap 20 over the frame 150 provides a second barrier of protection during and after the sterilization process. Alternatively, the frame 150 does not include a filter and the frame 150 is encompassed by the wrap 20 as shown in FIG. 12. In one configuration, the wrap 20 is sealed to the base via seal 86. A seal may be, alternatively, or additionally, be formed by applying a clamp 112 to the outside of the wrap 20, around the base 10 in channel 76.

It should be appreciated that including vents within the volume defined by the sterilizing wrap system 100 effects the venting pass through area to volume ratio. Exemplary embodiments of the sterilizing wrap system 100 can include one or more vents. The high venting pass through area to volume ratio affects the drying time required after the sterilization cycle and increases the surface area easily exposed to the sterilizing agent.

As shown in FIG. 13, the sterilization wrap 20 may take many different shapes and forms, including but not limited to a bag 92 defining a cavity. The sterilization wrap 20 may be sealed to itself or the base 10. The bag 92 may include a flexible collar 84 for expanding to dispose the wrap 20 over the sealing surface 60 of the base 10 during the deployment process and applying tension to the sealing surface 60 of the base 10 in the deployed position. The flexible collar 84 may include an elastic band for cinching the material to the base 10. In an alternative configuration, the wrap 20 does not include a flexible collar.

To maintain a sealed interface between the sterilizing wrap 20 and the sealing surface 60 of the base 10, a clamp 112 can be placed over the wrap 20. For example, a security band may be received by channel 76 on the base 10 as described supra to form a seal that provides a barrier to entry of bacteria and particles. Alternatively, or additionally, shrink wrap or Krayton material may be used to form the clamp around the base 10 such that a sealed interface is maintained between the wrap 20 and the base 10.

Moreover, the wrap 20 may alternatively, or additionally, include a seal 86 for forming a sealed interface between the wrap 20 and a sealing surface 60. The seal 86 may be formed of any seal that is capable of providing a sealed interface between the wrap 20 and the base 10, including but not limited to, a band, adhesive, sealant polymer, and tape. In another configuration, shrink-wrap is wrapped around the base 10 and then shrunk during the sterilization process as a result of the high heat created during the sterilization cycle. A seal between the wrap 20 and the base 10 is thus formed. Alternatively, heat may be applied before sterilization to shrink the shrink-wrap to secure the wrap 20 to the base 10 and to form a seal between the wrap 20 and the base 10 before sterilization.

As shown in FIG. 14, the base 10 may comprise a single surface 42 or table 40 with a wrap 20 configured as a sheet 182 forming a seal along a perimeter edge of the support surface 42 or along sealing surface 60. An additional seal may be maintained by including a clamp 112, such as a security band or the like. In one configuration, base 10 is partially covered, wherein a portion of the base remains uncovered and a portion of the base 10 has a wrap 20 sealed to the sealing surface 60 of the base 10.

Figure 19:
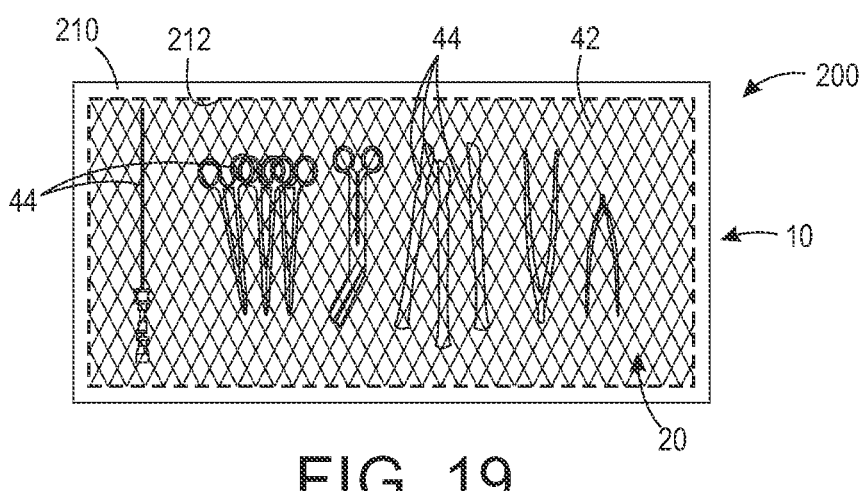
FIG. 19 is a top view of a base having a support surface for receiving objects requiring sterilization and a wrap sealed to a perimeter edge of the support surface.
Figure 20:
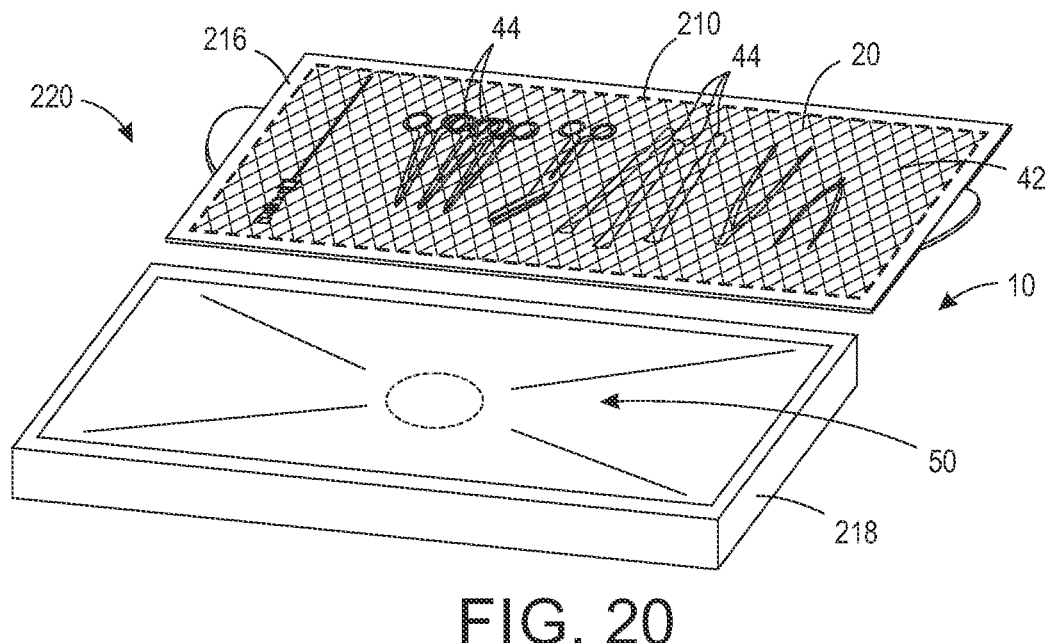
FIG. 20 is a perspective view of a base having a removeable support surface for receiving objects requiring sterilization and a wrap sealed to a perimeter edge of the support surface.
Figure 21:
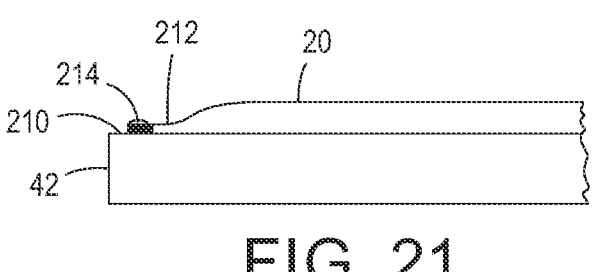
FIG. 21 is a cross-sectional view of a base having a wrap sealed to the support surface.
Figure 22:
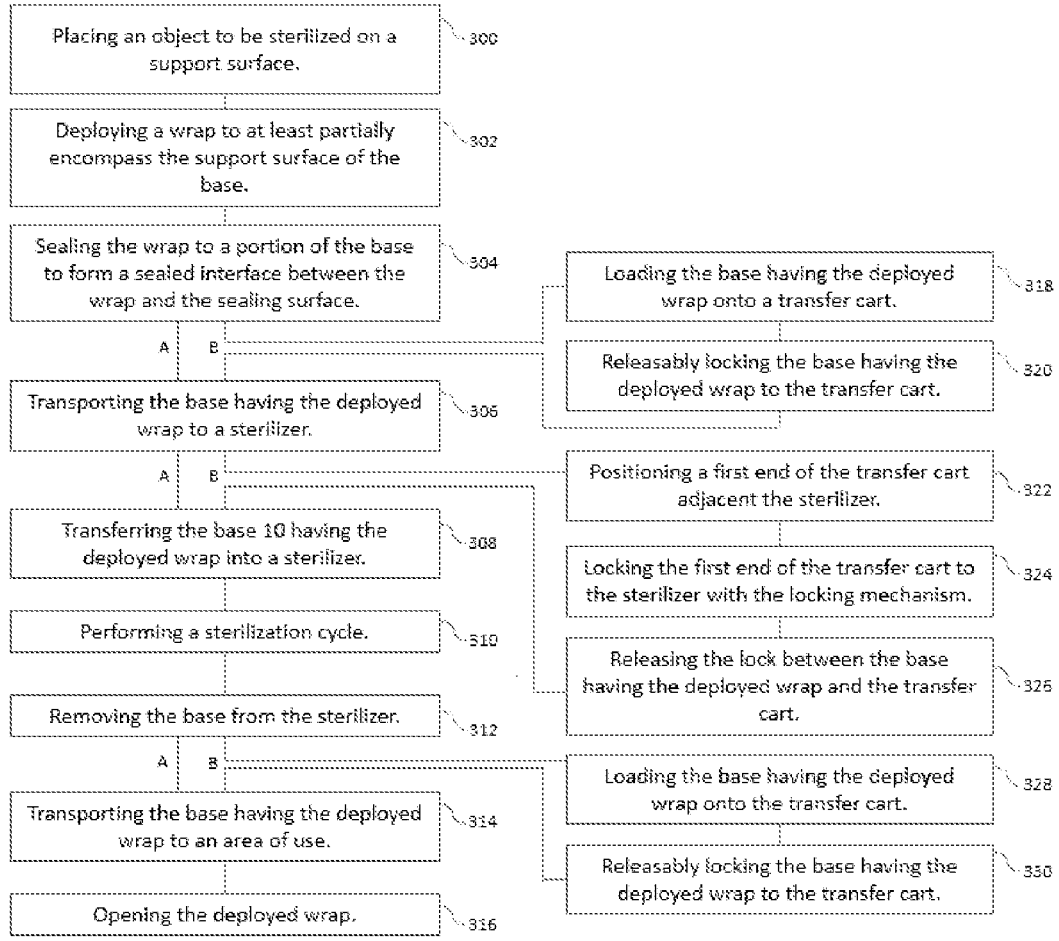
FIG. 22 is a flow chart disclosing the method steps of packaging objects for sterilization.

In an alternative configuration, as shown in FIGS. 19-21, the wrap system 200 may be a single-use wrap system having a wrap 20 and a rigid base 10 formed of a material adapted to withstand exposure to a sterilizing agent without degradation. The base 10 may be a table 40 having a flat support surface 42 for retaining objects 44 and a perimeter edge 210. The support surface 42 and the perimeter edge 210 of the base 10, in this configuration, are in the same plane, wherein the perimeter edge 210 provides a sealing interface. In one configuration, the sealing interface is continuous around the entire perimeter of the support surface 42. In another configuration, the perimeter of the support surface 42 includes spaces of non-sealed surfaces and sealed interfaces. In another configuration, the support surface 42 includes more than one wrap 20, wherein each wrap 20 is sealed to a particular area on the support surface 42. A wrap 20 sized to at least partially overlap the support surface 42 includes a perimeter edge 212 corresponding with the perimeter edge 210 of the support surface 42 of the base 10. The wrap 20 includes a sealant 214 for sealing the perimeter 212 edge of the wrap 20 to the perimeter edge 210 of the base 10. The sealant 214 may include, but is not limited to tape, adhesive, or sealant polymer. As shown in FIG. 22, the wrap system 220 may include a base 10 having a removeable flat support surface 42 for holding the objects 44. In this configuration, the support surface 42 may be a removable holder or plate coupled with the lower unit 218. The support surface 42 may be fenestrated or perforated to allow steam to enter and be released. The support surface 42 may further lock, fasten, nest or otherwise engage the lower unit 10. The lower under 10 may further include a drain system 50 as described supra.

In a configuration, the base 10 includes a locking mechanism to releasably lock the base to a base pedestal, legs, or transfer cart 192. The transfer cart 192 may comprise a frame 252, push handles 254, and wheels 256. If the transfer cart 192 is serving as an operating back room table, the transfer cart 192 may optionally not include push handles 254 or a locking mechanism. The transfer cart 192 can be constructed out of any durable material that is strong enough to maintain its shape and form under significant weight and also able to be sterilized. Ideally, transfer cart 192 is constructed out of a steel or aluminum alloy or a combination thereof. It should be understood that transfer cart 192 is merely an exemplary embodiment of a transfer cart 192.

The transfer cart 192 may further include a sled (not shown) having wheels 260 for sliding along transfer cart 192 guiderails when the sled and base 10 are loaded into a sterilizer. The transfer cart 192 is rigid enough to maintain the weight of the base 10 and sled or other like sterilizing device or apparatus. In one configuration, the base 10 releasably locks to the sled via a locking mechanism 262. The locking mechanism 262 provides a means to removeably affix the base 10 to the transfer cart 192. Exemplary embodiments of the locking mechanism 262 include any means that would allow a base to be securely affixed to a transfer cart 192, for example, a sled of the transfer cart 192, such that the base 10 only moves when transfer cart 192 moves. Additionally, the sled may releasably lock to the transfer cart 192 via a locking mechanism 262, which provides means to removeably affix the sled to the transfer cart 192. Exemplary embodiments of the locking mechanism 262 include any means that would allow a sled to be securely affixed to the transfer cart 192 such that the sled only moves when transfer cart 192 moves. The transfer cart 192 may further include a locking mechanism to releasably lock the transfer cart 192 to the sterilizer. Thus, the transfer cart 192 can be locked relative to the sterilizer when the sled and/or base 10 is loaded into the sterilizer to prevent unwanted movement of the transfer cart 192 during the weight transfer of the load from the transfer cart 192 to the sterilizer. Exemplary embodiments of the locking mechanisms include clamps, laches, slots, bolts, screws, and the like.

Push handles 254 of transfer cart 192 provide the means for a user to more easily push and pull transfer cart 192. Push handles 254 may be provided on opposite sides of transfer cart 192. Each of the push handles 254 span the width of transfer cart 192. It should be appreciated, that embodiments of push handles 254 include push handles 254 being located on all sides or only on one side of transfer cart 192 along with different configurations.

One advantage of having the base 10, such as an operating room back table, loaded directly onto the transfer cart 192 and then into a sterilizer is that once the sterilization cycle is complete, the base 10 (table) can be loaded back onto the transfer cart 192 and transferred directly to the operating room for use again. The instruments or other object, having already been organized on the tray before sterilization, are ready for use without further processing or organizing. In an alternative configuration, the base 10 and transfer cart 192 are loaded together into a ground-loading sterilizer. In this configuration, the transfer cart 192, the base 10, and the instruments contained thereon are sterilized in the ground-loading sterilizer. Thus, the base 10 is not separated from the transfer cart 192 during sterilization or during transportation.

The following steps may be followed with packaging objects for sterilization as shown in FIG. 22. First, according to step 300, at least one object to be sterilized is placed on a support surface of a base 10, which has at least one sealing surface 60, 70. A wrap 20 is deployed to at least partially encompass the support surface of the base 10 according to step 302. The wrap 20, in one configuration, includes a first portion 80 for encompassing the support surface of the base 10 and a second portion 82 for confronting the sealing surface 70 of the base 10. According to step 304, the wrap 20 is sealed to a portion of the base 10. In one configuration, the second portion 82 of the wrap 20 is clamped to the sealing surface of the base 10 to form a sealed interface between the wrap 20 and the sealing surface 70 in a deployed position. The method may further comprise transporting the base 10 having the deployed wrap 20 to a sterilizer 258 according to step 306. In one configuration, the base is transported according to route A, wherein the base 10 is hand-carried or transferred on another device. In another configuration, the base 10 is transported according to route B, wherein the base 10 is transferred on a transport cart having a releasable lock for locking the base to the transfer cart. According to step 308, the base 10 having the deployed wrap 20 is transferred into the sterilizer 258 and a sterilization cycle is performed in the sterilization cycle according to step 310. The method further includes removing the base 10 having the deployed wrap 20 from the sterilizer 258 according to step 312, transporting the base 10 having the deployed wrap 20 to the area of use according to step 314, and opening the deployed wrap 20 to expose the at least one object sterilized in the sterilizer 258, according to step 316. In one configuration, the wrap 20 may be opened by opening the first portion of the deployed wrap 20 along a set of predetermined guidelines to form wrap segments having an outer surface and an inner sterilized surface and folding the wrap segments over the first sealing surface exposing the inner sterilized surface. The step of transporting the base 10 having the deployed wrap 20 to the sterilizer 258 may further comprise in certain configurations, the steps of loading the base 10 having the deployed wrap 20 onto a transfer cart, the transfer cart having a first end including a locking mechanism and a second end, according to step 318, releasably locking the base having the deployed wrap to the transfer cart, according to step 320, positioning the first end of the transfer cart adjacent the sterilizer 258 according to step 322, and locking the first end of the transfer cart to the sterilizer 258 with the locking mechanism according to step 324 and releasing the lock between the base 10 having the deployed wrap 20 and the transfer cart to enable the base 10 having the deployed wrap to be transferred into the sterilizer 258 according to step 326. Upon completion of the sterilization cycle performed according to step 310, the base may be removed from the sterilizer 258 according to step 312 and loaded bac onto the transfer cart according to step 328. The base may then be releasably locked to the transfer cart according to step 330 and transported to the area of use according to step 314.

The present invention contemplates that many changes and modifications may be made. Therefore, while the presently-preferred form of the apparatus and method has been shown and described, and several modifications and alternatives discussed, persons skilled in the art will readily appreciate that various additional changes and modifications may be made without departing from the scope of the invention, as defined and differentiated by the following claims.

The invention claimed is:

1. A sterilizing wrap system comprising:

a base having a support surface and a first sealing surface, the support surface configured to support at least one object requiring sterilization;

a wrap sized to overlie the first sealing surface of the base and the object requiring sterilization to define a volume encompassing the support surface and the spaced first sealing surface of the base; and a first seal for maintaining a sealed interface between the wrap and the first sealing surface, wherein the wrap includes a first portion of a first material having an area for encompassing at least the support surface, and a second portion of a second material having an area for encompassing at least the first sealing surface of the base.

2. The sterilizing wrap system of claim 1, wherein the first seal is a clamp, and wherein the first sealing surface of the base is a channel at least partially extending circumferentially around the base, wherein the channel is sized to receive the clamp.

3. The sterilizing wrap system of claim 1, wherein the base further comprises a second sealing surface spaced from the first sealing surface, and wherein the wrap includes a second seal for forming a sealed interface between the wrap and the second sealing surface.

4. The sterilizing wrap system of claim 1, wherein the wrap is a bag formed of the first material, the bag having a flexible collar comprising the second material for expanding to dispose the wrap over the first sealing surface of the base in an install position and for applying tension to the first sealing surface of the base in a deployed position.

5. The sterilizing wrap system of claim 1, wherein the first material is a filter material and the second material is a flexible material.

6. The sterilizing wrap system of claim 5, wherein the second material forms the first seal, wherein the first seal is a clamp for maintaining the sealed interface between the wrap and the first sealing surface.

7. The sterilizing wrap system of claim 2, wherein the base is an operating room back table and wherein the base includes a skirt, the skirt having the channel for receiving the clamp.

8. The sterilizing wrap system of claim 1, wherein the support surface is a first portion of the base.

9. The sterilizing wrap system of claim 1, wherein the base further comprises wrap supports extending from the base, the wrap supports being at least one of collapsible and removeable.

10. The sterilizing wrap system of claim 8, wherein the first portion of the base is a tray configured to hold at least one of surgical instruments, or wherein the first portion of the base comprises trays, racks, frames, or shelves configured to hold instruments.

11. The sterilizing wrap system of claim 9 wherein the wrap supports include sidewalls and a top shelf spaced from the support surface of the base.

12. The sterilizing wrap system of claim 8, further comprising a frame operatively connected to the base, the frame having a plurality of struts forming front, back, top, and side portions, wherein the front, back, top, and side portions define a hollow center portion.

13. The sterilizing wrap system of claim 12, wherein the frame is removeable from the base.

14. The sterilizing wrap system of claim 1, wherein the support surface of the base is sloped.

15. The sterilizing wrap system of claim 1, wherein the support surface or at least one of the first and a second sealing surfaces of the base includes a drain.

16. A single-use sterilizing wrap system for use in the sterilization of objects requiring sterilization, the system comprising:

(a) a rigid base formed of a material adapted to withstand exposure to a sterilizing agent without degradation, the base having a support surface having a portion for retaining objects a perimeter edge, and a first sealing surface on at least one of the support surface or the perimeter edge;

(b) a wrap sized to overlap the support surface and having a perimeter edge corresponding with the perimeter edge of the support surface of the base; and (c) a sealing interface between the wrap and the first sealing surface configured to form, a seal between the wrap and the base, wherein the wrap includes a first portion of a first material having an area for encompassing at least the support surface, and a second portion of a second material having an area for encompassing at least the first sealing surface of the base.

17. The single-use sterilizing wrap system of claim 16, further comprising a holder for maintaining the objects, wherein the holder is removeable from the base.

18. The sterilizing wrap system of claim 1, wherein the sealed interface is configured to form a continuous seal between the wrap and the first sealing surface.

19. The sterilizing wrap system of claim 16, wherein the seal is a continuous seal between the wrap and the first sealing surface.

20. The sterilizing wrap system of claim 16, wherein the base is configured to drain at least one of sterilizing agent and liquid condensate from the base.

21. The sterilizing wrap system of claim 16, further comprising a drain system in the base, the drain system including at least one aperture having at least one filter.

* * * * *